United States Patent [19]

Morlino

[11] 4,185,087
[45] Jan. 22, 1980

[54] HAIR CONDITIONING COMPOSITIONS CONTAINING DIALKYLAMINO HYDROXY ORGANOSILICON COMPOUNDS AND THEIR DERIVATIVES

[75] Inventor: Robert J. Morlino, Port Chester, N.Y.

[73] Assignee: Union Carbide Corporation, New York, N.Y.

[21] Appl. No.: 865,128

[22] Filed: Dec. 28, 1977

[51] Int. Cl.$^2$ .............................................. A61K 7/06
[52] U.S. Cl. ............................... 424/70; 252/DIG. 2; 252/DIG. 3; 252/DIG. 13; 260/29.2 M; 424/DIG. 2; 424/78; 424/180
[58] Field of Search ............. 424/70, 180, 78, DIG. 2; 260/29.2 M, 46.5 E; 252/DIG. 13, DIG. 2, DIG. 3

[56] References Cited

U.S. PATENT DOCUMENTS

| | | | |
|---|---|---|---|
| 3,208,911 | 9/1965 | Oppliger | 424/70 |
| 3,248,296 | 4/1966 | Steinbach et al. | 424/70 |
| 3,389,160 | 6/1968 | Reid | 260/46.5 E |
| 3,964,500 | 6/1976 | Drakoff | 424/70 |

OTHER PUBLICATIONS

De Navarre, The Chemistry and Manufacture of Cosmetics, 2nd Ed., Continental Press, vol. IV, p. 1102, Florida.
Balsam et al., Cosmetics Science and Technology, vol. 2, pp. 365-372, Wiley-Interscience, New York, (1972).

*Primary Examiner*—James O. Thomas, Jr.
*Assistant Examiner*—Vera C. Clarke
*Attorney, Agent, or Firm*—Stanley Ktorides

[57] ABSTRACT

Hair care compositions containing one or more quaternary nitrogen derivatives of trialkylamino hydroxy organosilicon compounds have superior conditioning capability for hair.

16 Claims, No Drawings

HAIR CONDITIONING COMPOSITIONS CONTAINING DIALKYLAMINO HYDROXY ORGANOSILICON COMPOUNDS AND THEIR DERIVATIVES

BACKGROUND OF THE INVENTION

This invention relates to hair care compositions. More particularly, this invention relates to hair conditioning compositions which are especially useful for conditioning hair by leaving it in a pleasing and satisfactory, soft, lustrous and easily manageable condition. In a more specific aspect, this invention relates to aqueous, homogenous and conditioning shampoo compositions which exhibit outstanding cleaning characteristics, as well as being characterized by an outstanding capacity for conditioning cleaned hair.

It is well known that simple aqueous detergent compositions are useful for the cleansing of hair by promoting the removal of soil and excess natural oil. For practical use shampoo compositions must not dull the hair by removing all of the natural oils from the hair nor damage it by harsh detergent action. In addition, it must provide lather in both hard and soft water and be sufficiently stable so that it does not deteriorate on standing or in the course of normal use. In most detergent compositions now in use the removal of natural oils to a greater or lesser extent is unavoidable as a part of the cleansing action, as is some hair damage as a result of the action of detergent. Furthermore, shampoo compositions which thoroughly clean the hair usually leave it in a statically electrified state, in which the individual hairs repel each other, or in a state in which simple combing produces this undesired electrification. In either case, the hair is very difficult to manage. To overcome these defects, chemists in the field of hair treatment have vigorously explored alternative or complementary shampoo and hair conditioning systems. For example, in many conventional shampoo compositions, it is customary to include an additive such as a lanolin derivative, glycol, fatty esters or protein in an effort to condition the hair by replacing the stripped oils so as to leave the hair more manageable and natural after shampooing. Unfortunately, when these derivatives are incorporated directly into a shampoo, they may cause a loss of sudsing, sheen, and leave the hair with a sticky and unnatural feeling. Alternatively, a variety of products such as cream rinses, conditioners, weave sets and hair sprays, containing antistatic agents, conditioning agents and the like, have been developed for use after shampooing to counteract the adverse effects of shampooing on the hair and to return its sheen, combability and wave set retention and to reduce flyaway hair. It is obvious that the use of these additional materials is naturally necessarily expensive and requires additional time and effort involving additional application and treatment of the hair on the part of the users.

It is an object of this invention to provide a hair conditioning composition which may be used subsequent to shampooing or, alternatively, may be used in conjunction with a detergent in a shampoo composition.

It is an additional object of this invention to provide a stable conditioning shampoo composition to be used without a subsequent conditioning treatment.

It is further an object of this invention to provide a conditioning shampoo composition which exhibits excellent cleansing and lathering properties along with excellent conditioning properties to impart sheen, manageability and wave set retention to the cleansed hair.

It is another object of this invention to provide a post-shampooing composition which conditions hair by leaving it in a pleasing and satisfactory, soft, lustrous and easily manageable condition.

Other objects and advantages will become readily apparent from the following description and appended claims.

SUMMARY OF THE INVENTION

We have now discovered that compositions containing one or more quaternary nitrogen derivatives of trialkylamino hydroxy organosilicon compounds exhibit superior conditioning capability for the hair. The compositions of this invention leave the hair lustrous and pleasant to the touch. These compositions also reduce or entirely eliminate the snarling of wet hair which ordinarily results as the users fingers become entangled with the hair during the shampooing process. In addition, the compositions of the present invention promotes easy wet combing of the washed and rinsed hair, so that the hair shafts slip easily on each other and past the comb. They also promote easy dry combing and the reduction of static electrification of the hair. Thus, there is minimal drag on the comb and the strands of hair do not tend to fly away and become disaligned as a result of the dry combing process.

The aqueous hair conditioning compositions of this invention comprise:
 A. From about 0.1 to about 10.0 weight percent of a quaternary nitrogen derivative of a trialkylamino hydroxy organosilicon compound; and
 B. From about 75 to about 99.9 weight percent water.
 C. From about 0 to about 30 weight percent of one or more surfactants selected from the group consisting of amphoteric, polar non-ionic, anionic, cationic, non-ionic, zwitterionic surfactants or a combination thereof.

All weight percents are based on the total weight of the composition. As optional ingredients, the composition may also include other conditioning agents known to those of skill in the art.

DESCRIPTION OF THE PREFERRED EMBODIMENT

The essential components of the conditioning composition of this invention are quaternary nitrogen derivatives of trialkylamino hydroxy organosilicon compounds which corresponds to the formula:

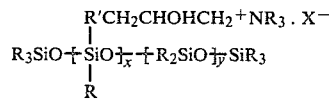

wherein:
 R is a monovalent hydrocarbon radical having from 1 to 18 carbon atoms;
 R' is a divalent hydrocarbon radical having from 1 to 18 carbon atoms as a divalent hydrocarbonoxy radical having from 1 to 18 carbon atoms wherein the oxygen of said hydrocarbonoxy radical is in the form of an ether linkage.
 X⁻ is halide anion;
 x has an average value of from 2 to 20;
 y has an average value of from 20 to 200.

It should be observed in the above generic formula that various R groups need not be identical. The structural representation is intended to show each individual R' group may be the same or different.

Suitable monovalent hydrocarbon groups represented by R in the structural representation set forth hereinabove include alkyl, alkenyl, aryl, alkaryl, aralkyl or like groups. Illustrative of more specific R groups or methyl, ethyl, propyl, butyl, isobutyl, decyl, octadecyl, cyclopentyl, cyclohexyl, naphthyl, vinyl, butenyl, cyclohexenyl, tolyl, xylyl, benzyl, and betaphenylethyl.

Suitable divalent hydrocarbon groups which are represented by R are alkylene, arylene or aralkylene radicals. Suitable divalent hydrocarbonoxy radicals represented by R' are the same as the permissible hydrocarbon radicals except that they contain one or more ether linkage, that is a functional unit of the formula, —CH$_2$OCH$_2$—. Illustrative of R' groups are methylene, ethylene, propylene, butylene, phenylene, phenylmethylene, methylphenylene or any of the aforementioned groups having one or more ether linkages incorporated within the basic structure.

The preferred and particularly efficacious quaternary trialkylamino hydroxy organosilicon derivatives for use in the compositions of this invention are those of the formula:

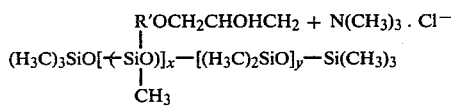

wherein:

R' is divalent alkylene having from 1 to 8 carbon atoms;

x has an average value of from 2 to 8;

y has an average value of from 20 to 50.

The quaternary trialkylamino hydroxy organosilicon derivatives employed in the compositions of this invention are known compounds that can be prepared by known methods known to those skilled in the art. For example, these compounds can be conveniently prepared by the method disclosed in U.S. Pat. No. 3,389,160.

The composition of this invention may also include as an optional ingredient from 9 to about 30 weight percent of one or more surfactants, i.e. detergents, selected from the group consisting of amphoteric anionic, cationic, polar non-ionic, non-ionic, zwitterionic surfactants or a mixture thereof to form a shampoo composition. Amphoteric, polar non-ionic, non-ionic and zwitterionic surfactants are prepferred for use in the composition of this invention. This surfactant functions as a lathering and cleansing agent.

By polar non-ionic detergent is meant a detergent in which the hydrophilic group contains a semi-polar bond directly between two atoms, e.g. N→O, P→O, As→O, and S→O. There is charge separation between the two directly bonded atoms, but the detergent molecule bears no net charge and does not dissociate into ions at neutral pH.

The polar non-ionic detergents which can be used in conjunction with or as an alternative to the amphoteric detergent includes open-chain aliphatic amine oxides of the general formula $R_1R_2R_3N \rightarrow O$. The arrow is a conventional representation of a semi-polar bond. These compounds are generally prepared by the direct oxidation of the appropriate tertiary amine. When $R_1$ is a much longer chain than $R_2$ and $R_3$, the amine oxides have surface activity. For the purpose of this invention, $R_1$ is an alkyl, alkenyl or monohydroxyalkyl radical having from about 10 to about 16 carbon atoms. Desirable surface active properties are lost if $R_1$ is substantially less than about 10 carbon atoms and the compounds are insufficiently soluble if $R_1$ is greater than about 16 carbon atoms, $R_2$ and $R_3$ are each selected from the group consisting of methyl, ethyl, propyl, ethanol and propanol radicals. Preferably $R_1$ is a dodecyl radical or a mixture of dodecyl with decyl, tetradecyl and hexadecyl such that at least 50% of the radicals are dodecyl radicals. $R_2$ and $R_3$ are preferably methyl radicals. A preferred amine oxide for the purpose of this invention is a dodecyldimethylamine oxide.

Other operable polar non-ionic detergents are the open chain aliphatic phosphine oxides having the general formula $R_1R_2R_3P \rightarrow O$, wherein R is an alkyl, alkenyl or monohydroxyalkyl radical ranging in chain length from 10 to 18 carbon atoms, and $R_2$ and $R_3$ are each alkyl and monohydroxy-alkyl radicals containing from 1 to 3 carbon atoms. A preferred phosphine oxide is dodecyldimethyl phosphine oxides which together with a method of preparation is fully described by Yoke et al. in application Ser. No. 173,834, filed Feb. 16, 1952, now U.S. Pat. No. 3,304,330.

As hereinbefore stated, amphoteric detergents can be used in conjunction with or in place of the polar non-ionic detergents described above. As used herein, the term "amphoteric" is interchangeable with the term "ampholytic". Amphoteric detergents are well known in the art and many operable detergents of this class are disclosed by A. M. Schwartz, J. W. Perry and J. Birch in "Surface Active Agents and Detergents," Interscience Publishers, New York 1958, Vol. 2. Examples of suitable amphoteric detergents include, for example, alkyl betaiminodipropionates, RN(C$_2$H$_4$COOM)$_2$; alkyl beta-amino propionates, RN(H)C$_2$H$_4$COOM; and long chain imidazole derivatives having the general formula:

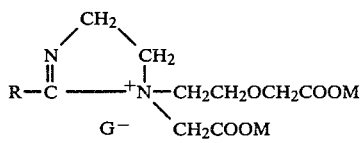

In each of the above formulae R is an acyclic hydrophobic group containing from about 8 to about 18 carbon atoms; G is $^-$OH or other anion or an acid salt or the salt of an anionic surface active sulfate or sulfonate and M is a cation to neutralize the charge of the anion. Specific operable amphoteric detergents include the disodium salt of lauroylcycloimidinium-1-ethoxyethionic acid-2-ethionic acid, dodecyl beta alanine, and the inner salt of 2-trimethylamino lauric acid. The substituted betaines and sultaines, such as alkyl ammonio acetates wherein the alkyl radical contains from about 12 to 18 carbon atoms can also be used. The betaine and sultaine types of ampholytic detergents are zwitterionic quaternary ammonium compounds having a general formula:

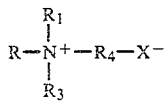

wherein $R_1$ is an alkyl having from about 10 to about 18 carbon atoms, $R_2$ and $R_3$ are each alkyl having from about 1 to about 3 carbon atoms, $R_4$ is an alkylene or hydroxyalkylene having from 1 to 4 carbon atoms, and X is an anion selected from the group consisting of $-SO_3^-$ and $-COO^-$.

Compounds which conform to the above general formula are characterized by the presence of both positive and negative charges which are internally neutralized (i.e. zwitterionic). When the anion X is $-SO_3^-$, these compounds are referred to as "sultaines." The term "betaines" is employed when the anion X is $-COO^-$. The following structural formulae are illustrative of the two types and their inner salt character.

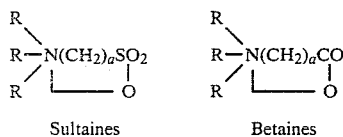

Sultaines  Betaines

When one R in the above formulae is a high weight alkyl having from about 10 to 18 carbon atoms, these compounds are surface active and have good detergency powers. If the high molecular weight alkyl contains less than about 10 carbon atoms, surface activity and detergency are inadequate. If this group contains more than about 18 carbon atoms, the compounds are not sufficiently soluble to be of utility in this invention. Preferably, the high molecular alkyl will contain from 12 to 16 carbon atoms or a mixture of dodecyl with decyl, tetradecyl, and hexadecyl radicals. A convenient source of a suitable mixture of alkyl groups is the middle cut of coconut fatty alcohol which has the approximate chain length composition: 2%-$C_{10}$, 66%-$C_{12}$, 23%-$C_{14}$, and 9%-$C_{16}$. Particular advantage can be gained by employing betaine or sultaines having an alkyl containing 16 carbon atoms in the compositions of this invention. The alkyl can, of course, contain one or more intermediate linkages such as ether or polyether linkages or non-functional substituents such as hydroxyl or halogen which do not substantially affect the hydrophobic character of the group.

Preferred compounds which fall within the above class include -1-(alkyldimethylammonio)acetate, 1-(alkyldimethylammonio)propane-3-sulfonate and 1-(alkyldimethylammonio)-2-hydroxy-propane-3-sulfonate wherein the alkyl contains from 12 to 16 carbon atoms.

The organic anionic detergent composition which may be included in the compositions of this invention may be either a water-soluble soap or a non-soap synthetic detergent or a mixture thereof.

Operable non-soap anionic organic detergents include, for example, water-soluble salts of organic sulfuric reaction products having in their molecular structure an alkyl group containing from about 8 to 20 carbon atoms and a radical selected from the group consisting of sulfuric acid ester and sulfonic acid radicals. Important examples of this type of non-soap anionic synthetic detergent, include the sodium or potassium alkyl sulfates, especially those derived by sulfation of higher alcohols produced by reduction of tallow of coconut oil glycerides; sodium or potassium alkyl benzene sulfonates, especially those of the types described by Guenther et al. in U.S. Pat. No. 2,220,099, granted Nov. 5, 1940, and by Lewis in U.S. Pat. No. 2,477,383, granted July 26, 1949, in which the alkyl group contains from about 9 to about 15 carbon atoms; sodium alkylglyceryl ether sulfonates, especially those ethers of higher alcohols obtained from tallow and coconut oil; sodium coconut oil fatty acid monoglyceride sulfates and sulfonates; sodium salts of sulfuric acid esters of the reaction product of one mole of a higher fatty alcohol (i.e. tallow or coconut oil alcohols) and about 3 moles of ethylene oxide; and others well known in the art, a number being specifically set forth in Byerly, U.S. Pat. Nos. 2,486,921 and 2,486,922.

Additional non-soap anionic organic synthetic detergents which can be used in this invention include the salts of the condensation products of fatty acids with sarcosine, i.e., acyl sarcosinate, wherein the acyl radical has a chain length range from about 10 to 18 carbon atoms. An especially preferred acyl sarcosinate for the purpose of this invention is sodium lauroyl sarcosinate.

Preferably, the non-soap anionic organic detergent will be of the high sudsing type as for example the alkylglyceryl-ether sulfonates, the sulfated fatty alcohols or the alkyl ether ethylene oxide sulfates wherein the ethylene oxide chain averages 3 units, and acyl sarcosinates, all as more fully set forth above. These and the foregoing detergents can be used in the form of their sodium, potassium or lower alkanolamine such as triethanolamine salts.

Conventional soaps may also be used as the anionic detergent component of this invention. Suitable soaps include the sodium, potassium, and lower alkanolamine salts of higher fatty acids of naturally occurring vegetable or animal fats and oils. For example, sodium, potassium and triethanolamine salts of fatty acids occurring in coconut oil, soybean oils, castor oil, tallow or synthetically produced fatty acids may be used.

Coconut, lauric and myristic mono- and diethanolamides may be used up to about 8% of the formula weight. The compounds serve to aid in the form stabilization of the polymer-detergent composition; however, they are not essential. Small quantities, up to about 5%, of non-ionic surfactants such as ethoxylated higher alcohols, alkyl phenols, and fatty acids may also be included as compatability agents and to promote rinsing.

The pH of the conditioning compositions of this invention may range from a pH of about 5.0 to a pH of about 8.0. Higher and lower pH values are undesirable because of their harsh properties which are detrimental to the hair and to their relative toxicity. The preferred formulations of this invention have a neutral pH of 7. Adjustment of the pH may be accomplished by the addition of non-toxic inorganic and organic acids, such as citric acid or phosphoric acid and bases such as triethanolamine and sodium or potassium hydroxide.

In addition to the essential ingredient, the compositions of this invention may include minor quantities of optional materials which are added for various specific purposes. Such other ingredients include, but are not limited to, medicaments, solvents, thickeners, perfumes, bactericides, sequestering agents, foam stabilizers, and opacifier, all of which are commonly used and are well known to be capable of use in hair care formulations.

The compositions of this invention may also include other conditioning agents.

The hair conditioning compositions of this invention can be conveniently prepared by a simple blending of the ingredients in the above indicated weight percents. The order of addition is not critical and will be determined solely on the basis of convenience.

The following examples are provided to more clearly illustrate this invention. In Examples I and II:

SILICONE-I: is a compound of the formula:

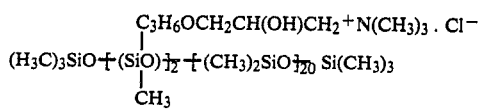

SILICONE-II: is a compound of the formula:

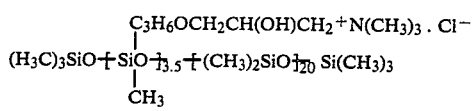

SILICONE-III: is a compound of the formula:

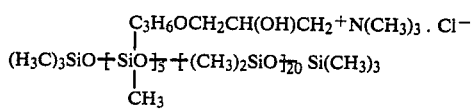

SILICONE IV: is a compound of the formula:

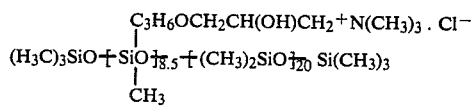

SILICONE V: is a compound of the formula:

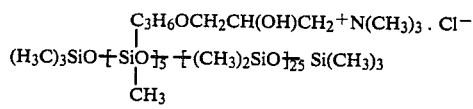

SILICONE VI: is a compound of the formula:

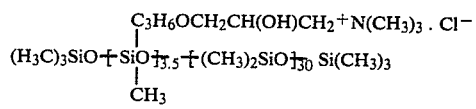

SILICONE VII:

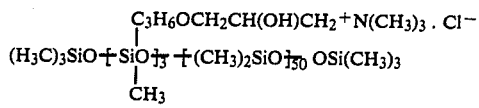

SILICONE VIII: is a compound of the formula:

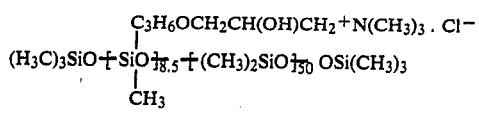

SILICONE IX: is a compound of the formula:

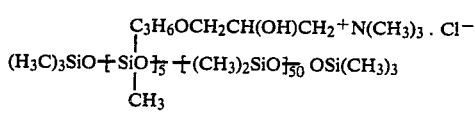

SILICONE X: is a compound of the formula:

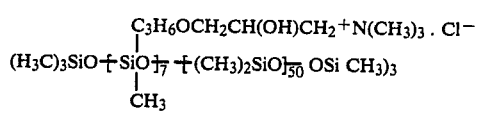

SILICONE XI: is a compound of the formula:

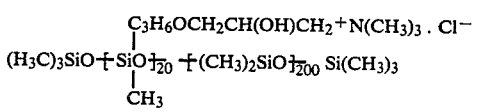

A number of compositions were prepared which illustrate the wide range of compositions possible in the practice of this invention. The percent by weight compositions of these composition are set forth in Table I. The compositions of Table I are conveniently prepared by simply mixing the quaternary trialkylamino hydroxy organosilicon derivative and water until complete dispersal is achieved followed by the addition of the optional ingredients with stirring until a uniform homogeneous mixture is achieved. Acid or alkali is added immediately after the addition of the detergent for pH adjustment, as desired and as required. Perfumes, dyes and preservatives are normally added after pH adjustment.

TABLE I

| INGREDIENT | COMPOSITIONS AND AMOUNTS BY WEIGHT PERCENT | | | | | | | | | | |
|---|---|---|---|---|---|---|---|---|---|---|---|
| | I | II | III | IV | V | VI | VII | VIII | IX | X | XI |
| I. QUATERNARY HYDROXYORGANOSILICONE | | | | | | | | | | | |
| 1 SILICONE I | 1.5 | — | — | — | — | — | — | — | — | — | — |
| 2 SILICONE II | — | 1.5 | — | — | — | — | — | — | — | — | — |
| 3 SILICONE III | — | — | 1.5 | — | — | — | — | — | — | — | — |
| 4 SILICONE IV | — | — | — | 1.5 | — | — | — | — | — | — | — |
| 5 SILICONE V | — | — | — | — | 1.5 | — | — | — | — | — | — |
| 6 SILICONE VI | — | — | — | — | — | 1.5 | — | — | — | — | — |
| 7 SILICONE VII | — | — | — | — | — | — | 1.5 | — | — | — | — |
| 8 SILICONE VIII | — | — | — | — | — | — | — | 1.5 | — | — | — |
| 9 SILICONE IX | — | — | — | — | — | — | — | — | 1.5 | — | — |
| 10 SILICONE X | — | — | — | — | — | — | — | — | — | 1.5 | — |
| 11 SILICONE XI | — | — | — | — | — | — | — | — | — | — | 1.5 |

TABLE I-continued

| INGREDIENT | COMPOSITIONS AND AMOUNTS BY WEIGHT PERCENT | | | | | | | | | | |
|---|---|---|---|---|---|---|---|---|---|---|---|
| | I | II | III | IV | V | VI | VII | VIII | IX | X | XI |
| II. WATER | 98.5 | 98.5 | 98.5 | 98.5 | 98.5 | 98.5 | 98.5 | 98.5 | 98.5 | 98.5 | 98.5 |

EXAMPLE II

Selected species of the conditioning compositions of this invention were evaluated to determine their performance in hair care applications. The compositions of this invention prepared in Example I were evaluated in creme rinse protocols, on both virgin brown hair and bleached hair. Evaluations of performance factors and test procedures were combability, fly-away, conditioning, overall feel and appearance.

TEST PROCEDURE FOR EVALUATION IN CREME RINSE APPLICATION SYSTEM

Two grams, ten inch tresses were prepared from both virgin brown Italian and bleached hair. (De Meo Brothers, New York, N.Y.) Each tress was wet with tap water and two grams of the control shampoo per two grams of tress was worked thoroughly through the hair. The tresses were rinsed with 40° C. tap water and the process repeated. The excess water was blotted from the tress using paper towels. One milliliter of the creme rinse lotion is applied to the hair and gently worked through the tress, taking care not to tangle or snarl the tress. The wet tresses were evaluated for feel and appearance. Using the wide tooth end of a black rubber comb, the tresses were combed. The length, in inches the comb traveled without meeting resistance was noted. This value is the wet combability. Each tress was hung individually and combed through. The procedure was carried out on three tresses. Using the wide tooth comb end, a black rubber comb was gently combed through each tress and the length, in inches, the comb travels without meeting resistance is noted. This value is the dry combability.

Each tress was vigorously combed ten times and the width of the bundle and the overall width of the fan (including single hairs) were measured in inches. These values are termed by flyaway.

TABLE II

| | PERFORMANCE ON VIRGIN BROWN HAIR | | | | | | | | | | |
|---|---|---|---|---|---|---|---|---|---|---|---|
| PROPERTY | COMPOSITION AND PERFORMANCE | | | | | | | | | | |
| | 1 | 2 | 3 | 4 | 5 | 6 | 7 | 8 | 9 | 10 | 11 |
| Wet Combability (in.)[1] | 3.4 | 6.2 | 6.2 | 4.2 | 4.2 | 3.9 | 6.2 | 4.2 | 4.4 | 5.4 | 3.0 |
| Wet Feel | sl. slippery | very slippery | very slippery | slippery | slippery | very slippery | very slippery | very slippery | slippery | very slippery | very slippery |
| Wet Appearance | sl. sheen | very good sheen | good sheen | good sheen | good sheen | good sheen | good sheen | good sheen | sheen | good sheen | good sheen |
| Dry Combability[2] | 1.0 | 0.4 | 1.2 | 1.0 | 1.0 | 0.3 | 1.2 | 0.3 | 1.2 | 0 | 0.3 |
| Dry Appearance | sheen | good sheen | very good sheen | very good sheen | very good sheen | good sheen | good sheen | good sheen | sheen | very good sheen | good sheen |
| Flyaway (in.)[3] | −0.5 | −0.2 | −0.5 | −0.5 | 0.7 | 0.5 | −0.3 | 0.5 | 0.3 | −0.3 | 0 |

[1] Number of inches over the control that the comb has traveled through wet hair.
[2] Number of inches over the control that the comb has traveled through dry hair.
[3] Number of inches that the flyaway has been reduced or increased compared to the control.

TABLE III

| | PERFORMANCE ON BLEACHED HAIR | | | | | | | | | | |
|---|---|---|---|---|---|---|---|---|---|---|---|
| PROPERTY | COMPOSITION AND PERFORMANCE | | | | | | | | | | |
| | 1 | 2 | 3 | 4 | 5 | 6 | 7 | 8 | 9 | 10 | 11 |
| Wet Combability (in.)[1] | 5.8 | 5.5 | 4.5 | 4.5 | 4.5 | 4.5 | 3.5 | 4.5 | 1.2 | 2.2 | 0.8 |
| Wet Feel | raspy | slippery | slippery | slippery | slippery | slippery | slippery | slippery | slippery | slippery | raspy |
| Wet Appearance | sl. sheen | sheen | sheen | good sheen | sl. sheen | sheen | good sheen | slippery | sheen | sheen | sl. dull |
| Dry Combability[2] | 5.7 | 5.4 | 2.7 | 2.3 | 2.3 | 1.3 | 5.7 | 1.6 | 5.7 | 4.4 | −0.4 |
| Dry Appearance | sheen | good sheen | v.good sheen | good sheen | good sheen | sheen | good sheen | good sheen | sheen | sl. sheen | good sheen |
| Flyaway (in.)[3] | −1.1 | −0.6 | −1.0 | −0.7 | −1.2 | −1.0 | −0.6 | −1.2 | −0.8 | −1.0 | −0.8 |

[1] Number of inches over the control that the comb has traveled through wet hair.
[2] Number of inches over the control that the comb has traveled through dry hair.
[3] Number of inches that the flyaway has been reduced or increased compared to the control.

The test results set forth in TABLES II and III illustrate the outstanding conditioning capacity of the composition of this invention in conventional application systems, shampoos, and creme rinse compositions. The tresses treated with the conditioning compositions of this invention exhibit outstanding luster and managability.

EXAMPLE III

A selected specie of this invention was evaluated in comparison with a known hair conditioning agent, in order to determine hair conditioning relative efficacy. The known hair conditioning agent selected for these studies was, Stearyl Dimethyl Benzyl Ammonium Chloride, "SB-25". The quaternary trialkylaminohydroxy organosilicon compounds selected for these studies was SILICONE II. The conditioning capacities of these compositions were determined on both virgin brown and bleached hair. Each composition was evaluated in a water solution at three concentration levels, 0.5, 1.5 and 3.0 weight percent based on the total weight of the water solution. The test procedures were as described in EXAMPLE II. The results of these tests are set forth in TABLE IV hereinbelow.

TABLE IV

| | SILICONE I | | | | | | SB-25 | | | | | |
|---|---|---|---|---|---|---|---|---|---|---|---|---|
| | VIRGIN BROWN HAIR | | | BLEACHED HAIR | | | VIRGIN BROWN HAIR | | | BLEACHED HAIR | | |
| PROPERTY | 0.5% | 1.5% | 3.0% | 0.5 | 1.5% | 3.0% | 0.5% | 1.5% | 3.0% | 0.5% | 1.5% | 3.0% |
| Wet Combability (in.)[1] | 10.00 | 10.0 | 9.7 | 9.3 | 9.7 | 9.7 | 9.5 | 9.3 | 10.0 | 7.0 | 8.7 | 5.0 |
| Dry Combability (in.)[2] | 10.0 | 10.0 | 9.7 | 9.7 | 10.0 | 10.0 | 9.0 | 10.0 | 10.0 | 9.3 | 9.7 | 7.3 |
| Flyaway, Inches[3] | 4.0 | 4.2 | 4.2 | 2.7 | 2.5 | 2.2 | 4.3 | 3.8 | 4.2 | 3.3 | 3.5 | 3.7 |

[1]Number of inches over the control that the comb has traveled through wet hair
[2]Number of inches over the control that the comb has traveled through dry hair
[3]Number of inches that the flyaway has been reduced or increased compared to the control The data set forth in TABLE IV illustrates the superior conditioning capacity of the compositions of this invention in comparison with known conditioning agents. For example, the performance of 0.5 weight percent of Silicone-I composition is equal to that of a 3.0 weight percent SB-25 solution on virgin brown hair in both wet combability and flyaway. On bleached hair, the SB-25 compositions failed to reach the performance level of a 0.5 weight percent Silicone I, composition regardless of the concentration level. The experimental data clearly indicates that a 0.5 weight percent SILICONE-I composition outperforms or at the least equals the performance of a 3.0 weight percent SB-25 composition. As such SILICONE-I is approximately six times more effective as a hair conditioning agent than SB-25. This high level of performance at low concentration levels results in considerably less build-up on the hair and, therefore, less oiliness.

What is claimed is:

1. A method of conditioning hair which comprises applying to said hair an effective amount of a composition containing:
   (A) From about 0.1 to about 10.0 weight percent of at least one compound of the formula:

$$R'-CH_2CH(OH)CH_2{}^+NR_3 \cdot X^-$$
$$R_3SiO(SiO)_x(R_2SiO)_ySiR_3$$
$$\quad\quad\quad\quad\; |$$
$$\quad\quad\quad\quad\; R$$

wherein:
   R is a monovalent hydrocarbon radical having from 1 to 18 carbon atoms;
   R' is a divalent alkylene radical having 1 to 18 carbon atoms or a divalent hydrocarbonoxy radical having from 1 to 18 carbon atoms wherein the oxygen in said hydrocarbonoxy radical is in the form of an ether linkage and wherein the hydrocarbon portion of said hydrocarbonoxy radical is present in the form of divalent alkylene radicals;
   $X^-$ is halide anion;
   x has an average value of from 2 to 20; and
   y has an average value of from 20 to 200;
   (B) From about 75 to about 99.9 percent water; and
   (C) From about 0 to about 30 weight percent of one or more amphoteric, cationic, anionic, non-ionic, polar non-ionic or zwitterionic surfactants.

2. A method according to claim 1 wherein R is alkyl.

3. A method according to claim 1 wherein R is methyl.

4. A method according to claim 1 wherein R' is alkylene having from 1 to 8 carbon atoms.

5. A method according to claim 1 wherein R' is a hydrocarbonoxy radical of the formula:

$$-C_3H_6OCH_2-.$$

6. A method according to claim 1 wherein $X^-$ is chloride anion.

7. A method according to claim 1 wherein x is from about 2 to about 8.

8. A method according to claim 1 wherein y is from about 20 to about 50.

9. A method according to claim 1 wherein (A) is a compound of the formula:

$$C_3H_6OCH_2CH(OH)CH_2{}^+N(CH_3)_3 \cdot Cl^-$$
$$(H_3C)_3SiO(SiO)_{3.5}[(CH_3)_2SiO]_{20}Si(CH_3)_3.$$
$$\quad\quad\quad\quad\; |$$
$$\quad\quad\quad\quad\; CH_3$$

10. An aqueous hair conditioning shampoo composition comprising:
   (A) From about 0.1 to about 10.0 weight percent of at least one compound of the formula:

$$R'-CH_2CH(OH)CH_2{}^+NR_3 \cdot X^-$$
$$R_3SiO(SiO)_x(R_2SiO)_ySiR_3$$
$$\quad\quad\quad\quad\; |$$
$$\quad\quad\quad\quad\; R$$

wherein:
   R is a monovalent hydrocarbon radical having from 1 to 18 carbon atoms;
   R' is a divalent alkylene radical having 1 to 18 carbon atoms or a divalent hydrocarbonoxy radical having from 1 to 18 carbon atoms wherein the oxygen in said hydrocarbonoxy radical is present in the form of ether linkages, and wherein the hydrocarbon portion of said hydrocarbonoxy radical is present in the form of divalent alkylene radicals;
   $X^-$ is halide anion;
   x has an average value of from about 2 to about 20; and y has an average value of from about 20 to 200;
(B) From about 75 to about 99.9 weight percent water; and
(C) From about 9 to about 30 weight percent of one or more amphoteric, cationic, anionic, non-ionic, polar non-ionic or zwitterionic surfactants.

11. An aqueous shampoo composition according to claim 10 wherein R is alkyl.

12. An aqueous shampoo composition according to claim 10 wherein R' is alkylene or hydrocarbonoxy having from 1 to 8 carbon atoms.

13. An aqueous shampoo composition according to claim 10 wherein x is from about 2 to about 8.

14. An aqueous shampoo composition according to claim 10 wherein y is from about 20 to about 50.

15. An aqueous shampoo composition according to claim 10 wherein (A) is a compound of the formula:

$$(H_3C)_3SiO(SiO)_{3.5}[(CH_3)_2SiO]_{20}Si(CH_3)_3$$
$$\underset{CH_3}{\overset{C_3H_6OCH_2CH(OH)CH_2{}^+N(CH_3)_3 \cdot Cl^-}{|}}$$

16. An aqueous shampoo composition according to claim 10 wherein $X^-$ is chloride anion.

* * * * *